US007015016B2

(12) United States Patent
Zagury

(10) Patent No.: US 7,015,016 B2
(45) Date of Patent: Mar. 21, 2006

(54) USE OF INACTIVATED IMMUNOSUPPRESSIVE OR ANGIOGENIC IMMUNOGENIC PROTEINS FOR PRODUCING SECRETORY IGA'S

(75) Inventor: Daniel Zagury, Paris (FR)

(73) Assignee: Neovacs, Paris (FR)

( * ) Notice: Subject to any disclaimer, the term of this patent is extended or adjusted under 35 U.S.C. 154(b) by 422 days.

(21) Appl. No.: 10/168,115

(22) PCT Filed: Dec. 14, 2000

(86) PCT No.: PCT/FR00/03526

§ 371 (c)(1),
(2), (4) Date: Jun. 17, 2002

(87) PCT Pub. No.: WO01/43771

PCT Pub. Date: Jun. 21, 2001

(65) Prior Publication Data

US 2003/0003106 A1    Jan. 2, 2003

(30) Foreign Application Priority Data

Dec. 15, 1999   (FR) .................................. 99 15825

(51) Int. Cl.
    *C12P 21/06* (2006.01)
(52) U.S. Cl. ........................... 435/69.1; 435/6; 435/7.1
(58) Field of Classification Search ............... 435/64.1, 435/6, 7.1
    See application file for complete search history.

(56) References Cited

FOREIGN PATENT DOCUMENTS

| WO | WO 96/27389 Y | 9/1996 |
|---|---|---|
| WO | WO 99/02712 X | 1/1999 |
| WO | WO 99/39735 Y | 8/1999 |
| WO | WO 00/03732 | * 1/2000 |

OTHER PUBLICATIONS

Murphy et al, Fields Virology, 2nd ED., 1990, Chapter 19, pp. 480-482.*
Ginkel et al, The Journal of Immunology, 2000, p. 4778-4782.*
Zhang et al (Journal of Virology, Oct. 2004, vol. 78, No. 19, 10249-10257.*
Girard et al, "New Prospects for the Development of a Vaccine Against Human Immunodeficiency Virus Type 1," Comptes Rendus de L'Academie des Sciences, Serie III. Sciences de la Vie, vol. 322, No11, Nov. 1999, pp. 959-966, France.
Boyaka et al. "Strategies for Mucosal Vaccine Development." America Journal of Tropical Medicine and Hygiene, vol. 60. No. 4 Supplement, Apr. 1999, pp. 35-45.
Montgomery et al, "Induction of Secretory and Serum Anitbody Responses Following Oral Administration of Antigen with Bioadhesive Degradable Starch Microparticles," Oral Microbiology and Immunology, vol. 13, No. 3, Jun. 1998, pp. 139-149.
Boyaka et al; "HIV Tat Protein Regulation of Mucosal Immunity," Journal of Human Virology, vol. 3, No. 5, Sep. 2000, pp 10-15.

* cited by examiner

Primary Examiner—Ali R. Salimi
(74) Attorney, Agent, or Firm—Browdy and Neimark, PLLC

(57) ABSTRACT

The invention concerns the use of a protein derived from cancel cells, cells infected by a virus or immune cells or an inactive fragment of said protein, said protein being initially an immunosuppressive and/or an angiogenic protein with local activity whereof said properties have been inactivated by at least 70% by a physical and/or chemical treatment, such as formolisation, carboxamidation, carboxymethylation, maleimidation or oxidation by oxygen bubbling, by genetic recombination or by adjuvant conditioning, said treatment preserving its property of being identified by antibodies directed against said protein, and preserving sufficient immunogenic properties for generating antibodies neutralizing or blocking said native protein, or the use of a DNA molecule corresponding to said protein inactivated by mutation or to said inactive fragment, for obtaining a medicine designed to provide a patient with mucosal immunity based on secretion of IgA secretory antibodies, pharmaceutical compositions for the mucous membranes and IgA antibodies.

6 Claims, No Drawings

USE OF INACTIVATED IMMUNOSUPPRESSIVE OR ANGIOGENIC IMMUNOGENIC PROTEINS FOR PRODUCING SECRETORY IGA'S

The present invention relates to the use of a protein originating from cancerous cells, from cells infected by a virus or immune cells, from a fragment of such a protein or also from a DNA molecule corresponding to said protein or fragment, for the preparation of a medicament intended to give a patient mucosal immunity based on the secretion of Secretory IgA's.

Active compounds to fight cancer, which is the major medical plague of our era, are still sought. A number of therapies have been developed with varying success as there is still a high mortality rate. These therapies were firstly surgical abscission for solid tumors, radiotherapy and chemotherapy. These therapies seem insufficient in a number of cancers for which no clinical success has been recorded indicating a significant prolonging of the life of the patients or their complete cure.

Cancers are proliferations of cells which can then spread in the body to form metastases. It is known that the immune system of a normal individual regularly eliminates nascent cancer cells (immunosurveillance concept), and that the formation of a cancer is associated 1) with evasion of the local immune surveillance system then with an advanced stage of cancer, with systemic immunosuppression and 2) with a proliferation of the vascular endothelial cells providing the nutrient supply to the tumor cells (neoangiogenesis).

Most of the anti-cancer agents (chemotherapy, radiotherapy) used to date combat the replication of cancerous cells. These agents do not target the particular environment necessary for the proliferation of cancerous cells, characterized both by the absence of local activity (paracrine) of the anti-tumor cell immune system (immune evasion) and by the appearance of intratumoral vascularisation (neoangiogenesis).

That is why, recently, new therapeutic approaches have been introduced. Some aim to stimulate the anti-tumor immune system by cell therapy or by the activation of genes coding for proteins stimulating the immune response (gene therapy) or also by immunising directly against antigens, identified as specific or associated antigens of the MAGE type tumor (vaccination). Others aim to combat neoangiogenesis, by using antimetabolites destroying the endothelial cells (Judah Folkman). In this new context it should be noted that De Bruijn et al., (Cancer Res. (1998) 58, pages 724–731) describe the use of native E6 and E7 proteins to induce a cytotoxic cell response (CTL) in mice to protect against the implantation of tumor cells.

The applicant has discovered with surprise, after lengthy research, that factors which are immunosuppressive or angiogenic to paracrine action are induced by tumors. These factors which are soluble can, on one hand, locally prevent the immune cells from acting effectively, even if they are stimulated (immunosuppression) and can, on the other hand, provide the nutrition for cancerous cells, by activating the proliferation of the endothelial cells (angiogenesis).

The phenomena evading the cellular immune defence of the host by inducing their paralysis in situ is a strategy used by a number of cancers and is necessary to their survival. Initially immunosuppression remains localised at the level of the tumor, as the individual is also capable of defending themselves against other aggressions such as infections. However at a later stage, this immunosuppression can spread, and become widespread, as attested by the spreading of metastasises and the extreme vulnerability of cancer patients faced with infections on top of the debilitating effects due to chemotherapy or radiotherapy. This evasion from the control of the immune system is due to a paralysis of the immune system (immunosuppression), which prevents it from functioning normally. This immunosuppression sets in motion paralysing factors, which are produced by cancerous cells or their environment. Therefore local paralysis of the cells of the immune system or immunosuppression represents a major weapon of cancerous cells which allows them to evade the host's immune system. Proteins released by the infected cells therefore act as veritable toxins on the surrounding immune cells, disturbing their mechanism and blocking in situ (in a paracrine manner) the cells of the immune system, protecting the infected cells.

Malign tumors are characterised by the presence of significant vascularisation, which provides a blood flow necessary for the nutrition of cancerous cells. This vascularisation is carried out by activation of the vascular endothelial cells induced on contact with the tumor cells (neoangiogenesis). The works of Judah Folkman have recently shown that controlling tumoral neoangiogenesis could represent an effective and decisive weapon against cancers (Folkman J., *Semin. Cancer Biol.*, 1992, 3 (2): 65–71).

In this physiopathological context, the Applicant has discovered, after lengthy research, in the case of ATL, cervical cancer, and kaposi sarcoma, three proteins involved in local immunosuppression at the level of the tumor: these are HTLV 1 Tax protein, Papilloma virus E7 protein, and HIV-1 Tat protein in kaposi sarcoma. In the latter, there is also as etiological agent a herpes virus (HHV8), which would explain why kaposi sarcoma also happens in subjects not infected by HIV-1. Tat is involved in kaposi sarcoma, but researchers have not identified its role of generating local immunosuppression which encourages the generation of kaposi sarcomas. Interestingly, the Applicant has found that some of these immunosuppressive proteins, such as HIV-1 Tat protein and HPV E7 protein (strains 16 and 18) also have activating effects on vascular endothelial cells.

To combat these immunosuppressive and/or angiogenic factors, the Applicant proposed to induce by general route the specific antibodies directed against these extra-cellular factors. It is in this way that she has described the administration of the aforementioned proteins by the two conventional routes for the administration of vaccines, namely the oral route and the injectable route.

In a previous Patent Application, the Applicant showed in this way how to block the soluble factors released by the tumor cells or infected by a virus by specific antibodies. By "soluble factors", is meant factors (generally proteins) synthesized by these cells and released in the extracellular medium either by active transport or by passive diffusion. The aforementioned extracellular factors can act in situ either by inhibiting the immune cell response, including the activation of the cytolytic T lymphocytes (CTL), either by disrupting the cytokine network, or by satisfying by neoangiogenesis the nutritional requirements of the tumor. These extracellular factors can be of cell origin (cytokines) or, for cancers induced by viruses or viral diseases, viral proteins, mainly regulatory proteins, present in the extracellular medium.

They have in particular described means making it possible to obtain, in the circulating medium, IgG class antibodies directed specifically against deleterious, for example immunosuppressive and/or angiogenic factors, said antibodies being likely to block these factors and neutralise the effects on the immune and/or endothelial cell. These specific IgG class antibodies were either induced by active immunisation (vaccination) directed against the proteins in particular the previously identified soluble factors, or administered passively (passive immunisation). The circulating antibodies, present in the extracellular medium, by combining with these proteins, can neutralise the undesirable effects.

The Applicant has identified such soluble factors in at least three virally induced cancers: kaposi sarcoma (HIV-1), cervical cancer (HPV) and ATL leukemia (HTLV-1 and -2) These 3 factors, all of viral origin, are the HIV-1 Tat protein, the HPV E7 protein and the HTLV-1 Tax protein respectively.

A number of cancers are induced by viruses such as HIV-1 responsible for kaposi sarcoma and other cancers, HPV at the origin of cervical cancer, HBV and EBV associated, respectively, with hepatoma and Burkitt's disease.

AIDS (Acquired Immune Deficiency Syndrome) caused by HIV-1 and characterized by generalised cell immunosuppression, can be manifested by kaposi sarcoma, vascular cancer, or by other forms of cancer including some leukemias or lymphomas. The cell immunosuppression observed in this disease which encourages the appearance of these cancers is induced by the HIV-1 regulatory Tat protein, which, if it does not belong to the virus's own structure, is released by the infected cells into the extracellular medium. In this extracellular form, the Tat protein, acting as a veritable viral toxin, exerts an immunosuppressive effect on the neighbouring immune cells (Zagury D. et al.; *PNAS*, 1998, 95: 3851–56). In addition, at the level of the kaposi sarcoma, it has been shown that the Tat protein associated with the inflammatory cytokines (IFNα, Il-1, TNFα) and with BFGF, encourages the neoangiogenesis which forms the tumor (Ensoli B. *J Virol* 1993, 67: 277–287).

In fact, by its immunosuppressive and angiogenic properties, the Tat protein, present in the extracellular medium in the disease AIDS encourages not only the development of kaposi sarcoma caused by the HHV8 virus, but also other cancers, including lymphomas or leukemias.

Epithelial cervical cancer is caused by some strains of the HPV virus (strains 16 and 18). Cancerous cells of this cancer only express 2 proteins in the early appearance of this virus, the E6 protein and the E7 protein which, both have effects on the regulatory factors of the cell cycle of the cancer cell. Moreover, the E7 protein, present in the extracellular medium, explains the appearance in patients of a low count of anti-E7 antibodies. The extracellular E7 protein, such as the extracellular Tat protein can act locally as a toxin on the stromal cells (lymphoid cells or endothelial cells) of the tumor.

This E7 protein has in fact shown immunosuppressive and angiogenic properties experimentally. The immunosuppression induced by the E7 protein was characterized by the inhibition of the proliferation of the T cells stimulated by PPD or tetanic toxoid, the inhibition of the proliferation of the T cells stimulated by allogenic cells, the overproduction of IFNα (immunosuppressive cytokine) by antigen presenting cells (APC). The angiogenic power of the E7 toxin on the endothelial cell cultures originating from the umbilical cord of new-borns and pre-treated with E7 protein was suggested by the following observations: formation of a number of cell nests, visible with phase contrast; identification by Facs of CAM markers (ICAM and VCAM) within endothelial cells and modification of the cytoskeleton of the cells in culture observed by immunofluorescence and alteration of the expression of the nitrogen monoxide synthetase inducible by the endothelial cells in culture, in the presence of the E7 protein. As can be seen more decisively in the examples, the angiogenic power of the E7 toxin can be directly demonstrated "in vitro" by the activation of the vascular endothelial cells originating from cell lines or from fresh cells from the umbilical cord of new-borns induced by the E7 protein of the HPV (strain 16).

Whilst carrying out this research, the Applicant realised that when cancer affecting an epithelial mucous membrane such as cervical cancer or also a viral infection affecting the genital, vaginal, intestinal or rectal mucous membranes was involved, it was important that the immune reaction intended to combat the disease can act locally, within these mucous membranes to block it at an early stage.

It would appear desirable therefore, to induce a mucosal immune reaction, generating secretory IgA class antibodies.

The induction of antibodies directed against the extracellular viral factors such as Tat, E7 or Tax proteins, like toxins on the stromal lymphoid or intratumoral endothelial cells, involves the preparation of immunogens biologically devoid of the deleterious effects of the native protein. Such immunogens or the specific antibodies that they induce can thanks to their properties combat the immunosuppression and/or the angiogenesis present within tumors and therefore be useful as anti-cancer medicaments. But the use of DNA molecules also makes it possible to attain this objective.

A subject of the present Application is mainly the use:
- of a product obtained from a natural protein which is modified by any known technique such as by chemical, physical route (including galenic form) or by genetic engineering, in such a way that its immunosuppressive properties are inactivated by at least 70%, preferably at least 90%, in particular at least 95%, by a chemical, physical treatment and/or by suitable genetic construction, even by a suitable presentation, or
- of a DNA molecule corresponding to said protein inactivated by mutation or to said inactive fragment, representing the toxoid version of the genetic vaccines (DNA vaccines).

for obtaining a medicament intended to give a patient mucosal immunity, based on the secretion of secretory IgA class antibodies.

A subject of the invention is also the use of secretory IgA class antibodies against an immunopathogen, in particular an immunosuppressive or angiogenic protein with local activity induced by a cancer cell or a cell infected by a virus, for obtaining a medicament intended for use as an anti-local immunosuppression agent and/or as an anti-angiogenic agent with local activity.

Given that cancers can proliferate thanks to the local immunosuppression referred to above and to angiogenesis, the above products are of use in part in obtaining a medicament intended for use as an anti-cancer medicament.

The aforementioned natural protein is characterized in that it is a protein which is initially immunosuppressive and/or angiogenic with local activity induced by cancerous cells or by cells infected by a virus or a fragment of these proteins.

That is why a subject of the present invention is the use of a protein originating from cancerous cells, cells infected by a virus or immune-system cell or also an inactive fragment of this protein, said protein being an initially immunosuppressive and/or angiogenic protein with local activity the properties of which are inactivated by at least 70%, preferably at least 90%, in particular at least 95%, by a physical and/or chemical treatment, such as formolation, carboxamidation, carboxymethylation, maleimidation or oxidation by oxygen bubbling, by genetic recombination or also by adjuvant conditioning, said treatment retaining its property of being recognized by antibodies directed against said protein, and retaining sufficient immunogen properties to generate antibodies neutralising or blocking said native protein, or also the use of a DNA molecule corresponding to said protein inactivated by mutation or to said inactive fragment, for obtaining a medicament intended to give mucosal immunity to a patient based on the secretion of IgA class antibodies.

By "anti-immunosuppression or anti-angiogenic agent" is meant that the agent can have the first, the second or both effects.

By "initially immunosuppressive and/or angiogenic locally acting protein" is meant that the native protein, i.e. before inactivation, produced the first, the second or both effects.

The inactivated proteins or inactive fragments of the present invention, sometimes called hereafter "inactivated proteins" or "toxoids", or DNA molecules generating the locally acting initially immunosuppressive and/or angiogenic protein inactivated by mutation and because of this presenting the toxoid by DNA vaccination (toxoid version of the DNA based genetic vaccines) make it possible to fight cancers by a specific and additional approach to those of the prior art and, targeting the paralysis of the immune system and/or also angiogenesis induced by extracellular substances produced locally around cancerous cells. This immune paralysis and/or angiogenesis constitutes a veritable protective barrier and/or a source of nutrition for the tumor.

The inactivated proteins, fragments or DNA molecules according to the present invention make it possible to combat firstly these immunosuppressive and/or angiogenic proteic factors, by mucosal formation of IgA class antibodies against these proteins and in particular against these soluble proteic factors to allow the immune system to act effectively and/or to thus block neoangiogenesis at the same place of entry of the infection or the location of the disease.

It is important to use the deleterious extracellular proteic factor in particular in physically, chemically and/or genetically modified (inactivated) and non-native (or natural) form so that it no longer exerts its harmful effects (paracrine paralysis of the immune system or local angiogenesis).

The physical treatments can be carried out by heat, U.V. radiation, X-rays or contact with an $O_2$ rich atmosphere. These physical treatments generating intramolecular modifications between chemical radicals (thiol groups for example), can in a suitable manner change the conformation of the molecule, functionally inactivate it whilst preserving its immnunogenic properties.

Chemical treatment can be carried out using a coupling agent such as a dialdehyde, or a carrier protein activated by pre-treatment preferably using a dialdehyde, or glutaraldehyde. Chemical treatment can be carried out by using a monoaldehyde, in particular formaldehyde. The teaching of WO-A-96/27389 can be referred to regarding this.

Chemical treatment can be carried out in particular by other processes such as carboxymethylation or carboxamidation. An example of the carboxymethylation technique is illustrated in WO-A-99/33872. Chemical treatment can also be carried out by N ethylmaleimidation combined or not combined with glutaraldehydation.

As an inactivation technique the reaction of at least one thiol function of the protein with ammonium 4-chloro-7-sulphobenzofurazane, N-[iodoethyl]-trifluoroacetamide or N-(6-[7-amino-4-methylcoumarin-3-acetamido]hexyl)-3'-(2'-pyridyldithio) propionamide as well as the reaction of at least one amino function of the protein with ethylacetimidate, an anhydride, 2-iminothiolane hydrochloride, N-succinimidyl S-acetylthioacetate, sulphosuccinimidyl acetate, sulphosuccinimidyl-4-O-[4,4'-dimethoxytrityl]butyrate, succinimidyl 7-amino-4-methylcoumarin-3-acetate, sulphosuccinimidyl 7-amino-4-methylcoumarin-3-acetate or phenylglyoxal can be mentioned.

The immunogen can be inactivated thanks to a galenic presentation within an oily liquid, such as Freund's incomplete adjuvant or also those likely to modify the non-covalent bonds (electrostatic forces, Van der Waals forces or hydrogen bonds) necessary for its toxic effects.

Genetic modifications can be obtained by genetic engineering carrying out insertions, deletions or substitutions of residues, operations intended to reduce or suppress the deleterious functional sites of the natural molecule. Genetic mutants can undergo or not undergo an additional chemical and/or physical treatment. The modified proteins above can for example be prepared from a protein having an identical or similar sequence to a peptide sequence of an immunopathogenic, in particular immunosuppressive or angiogenic protein, such as the HIV-1 Tat protein, the Papilloma virus E7 protein or the HTLV1 Tax protein or of a fragment of these proteins and be obtained for example by conventional peptide synthesis on resin or by genetic engineering. All of these processes are well known in the state of the art. The inactive but immunogenic mutants have at least one DNA molecule which codes for their production. Such DNA molecules are of particular interest in the present invention as can be seen hereafter.

In order to verify that the native immunosuppressive and/or angiogenic protein is properly recognised by antibodies directed against said modified immunosuppressive protein or its modified or non-modified protein according to the invention, verification of the formation of antigen-antibody complexes can for example be carried out immunologically by Elisa in the presence of specific antibodies.

In preferred conditions of implementation, the immunogenic compound originates from a native compound (protein or polypeptide fragment) treated with aldehyde, carboxamide, carboxymethyl, or maleimide.

In order to determine if the immnunogenic properties of the modified immunosuppressive and/or angiogenic protein or a fragment of this protein have been sufficiently preserved (that is to say if it has been inactivated but not denatured) to create antibodies blocking the effects of said native protein, immunisation of mammals (rabbits, rats, mice) using an immunogenic compound according to the invention and verification that the antibodies produced neutralise the immunosuppressive or angiogenic activities of the protein can for example be carried out, as will be seen for the HIV-1 Tat protein, Papilloma virus E7 protein and HTLV1 Tax protein in the experimental part.

In order to determine if the modified immunosuppressive protein or the fragment has lost at least the desired proportion of its immunosuppressive properties, the effect of the immunosuppressive protein on the immunosuppression of the mononucleated cells of human peripheral blood (PBMC) can for example be studied.

The DNA (plasmid with promoter) can be delivered to the mucosal surfaces in the form of Naked or formulated DNA, for example in the form of cationic or concentrated liposomes around gold particles or also in the form of microspheres. It is advantageously used in the presence of adjuvants in particular bacterial toxins such as CT (cholera toxin) or LT (*E. coli* labile enterotoxin). Such techniques of mucosal immunisation with DNA molecule based vaccines are in particular described in Microbes and Infection, 1999, 685–698 by McCluskie et al.

The immunosuppressive or modified angiogenic and immunogenic protein can be derived from any protein which is in particular immunosuppressive with local activity induced by tumors or in AIDS patients; the HIV-1 virus Tat protein, the Papilloma virus E7 protein or the HTLV1 virus Tax protein are particularly chosen. The mannan-dependent lectin produced by activated immune cells is also chosen.

By "are derived" or "to derive" from an immunopathogenic, in particular immunosuppressive or angiogenic protein with local activity produced by cells which are cancerous or infected by a virus or produced by immune cells, is meant that the immunogenic compound can be constituted by all or a fragment of the starting immunopathogenic, in particular immunosuppressive or angiogenic protein.

It can comprise one or more modifications in the amino acids of this protein or fragment such as deletions, substitutions, additions, or functionalisations such as acylation of amino acids, provided that these modifications remain within the specific context above (absence of toxicity, immunological character). For example, in general the replacement of a leucine residue with an isoleucine residue does not modify such properties; the modifications must generally concern less than 40% of amino acids, preferably less than 20% and more particularly less than 10% of the immunopathogenic, in particular immunosuppressive or angiogenic protein. It is important that the protein or modified fragment is not denatured as can occur for example by a physical treatment such as heat, in order to preserve its conformational sites so that the antibodies induced by the modified derivatives are active vis a vis the native protein.

In preferred conditions, the immunogenic compounds of the invention comprise at least 50% of all or a segment of the immunopathogenic, in particular immunosuppressive or angiogenic protein, preferably at least 70%, particularly at least 90%, and more particularly all or almost all of said immunosuppressive or angiogenic protein.

Generally speaking, as far as modifications are concerned, the homology or the similarity between the modified immunogen and the protein or part of the native immunosuppressive protein, as well as the size of the immunogenic compound, as well as the methods of use, or coupling the immunogenic compound according to the invention to an immunogenic protein such as tetanic toxoid, WO-A-86/06 414 or EP-A-0.220.273 or also PCT/US.86/00831 which are equivalents, can in particular be referred to, the teaching of which is incorporated here by way of reference.

An immunogenic compound as defined above is also preferred which is a product obtained by genetic recombination presenting a peptide homology of at least 70% with the HIV-1 Tat, HTLV1 or 2 Tax and HPV E7 proteins or the mannan-dependent lectin produced by activated immune cells or a segment of these proteins.

An immunogenic compound as defined above is also preferred, characterized in that it is treated with an aldehyde, and that it is a carboxamide, carboxymethyl or maleimide.

Finally an immunogenic compound as defined above is preferred, characterized by adjuvant conditioning which makes it biologically inactive, such as an oily emulsion in incomplete Freund's adjuvant (IFA).

A desired mutant homologous immunogenic compound can also be derived.

It should be remembered here that by galenic conditioning of a physiologically active protein, its biological activity can be masked whilst preserving its immunogenicity.

The carboxymethylation reaction makes it possible to modify the thiol groups (sulphhydryl groups) present at the level of the cysteine residue of the sequence of linked amino acids. Carboxymethylation inactivates some toxic functions dependent on the SH groups as reported for the Tat protein Frankel et al. Cell Vol 55 (1988).

Apart from carboxymethylation, carboxamidation or maleimidation can be used to block the SH groups and form S-carboxymethyl, S-carboxamide or S-maleimide complexes.

For example, the Tat protein has 7 cysteines. These cysteines participate in the formation of inter- and intrachain disulphide bridges and contribute to the formation of oligomers.

The product of the reaction is in each case a S-carboxymethylcysteinyl or S-carboxymethylamidocysteinyl residue.

A fragment can comprise from 8 to 110 amino acids for example, preferably from 12 to 60 amino acids and in particular from 12 to 40 amino acids. Such a fragment can also comprise C or N terminal ends of 1 to 5 additional amino acids i.e. different from the original segment. A fragment must moreover comprise at least one cysteine to be able to be for example the subject of carboxymethylation. The fragments, if they are chosen by preference to be inactivated by themselves, can in fact be subjected if desired to the same inactivation treatments as whole or almost whole proteins.

The above carboxymethylation reaction can also be carried out with other chemical agents such as performic acid, 3-bromopropionic acid, ethyleneimine, (2-bromoethyl) trimethylammonium bromide, 2-bromoethane sulphonate, 1,3-propanesulphone etc.

In preferred conditions for the implementation of the above-described process, said starting protein or fragment can be presented in the form fused to a marker (FP) or non-fused (P). The FP form can modify per se the molecular conformation and thereby modify its activity.

The starting proteins or fragments of the process are known products the inactivation processes of which may have been described in literature as in WO-A-99/33872. These starting proteins may even be commercially available (Immunodiagnostics Inc., Cat# 1002-2) or can be prepared in a conventional manner.

The above starting proteins or fragments can in particular be prepared by:
1) Synthesis by genetic engineering or by biochemical synthesis;
2) Purification The proteins produced by affinity chromatography can be purified by genetic engineering, using for example antibodies directed against the protein or one of its fragments; the protein fused to a marker (FP) which will serve in attachment to an affinity column can also be synthesized.

In other preferred conditions for the implementation of the above-described process, when the protein or fragment is fused to a marker (FP), it is subjected to:

- concentration, for example by ultrafiltration;
- desalting, for example, by gel filtration;
- treatment with cyanogen bromide or enterokinase to cleave the fusion protein and thus release the protein or fragment;
- concentration and diafiltration;
- cationic exchange chromatography;
- concentration by ultrafiltration, followed by filtration on exclusion gel.

The above reaction with cyanogen bromide makes it possible to cleave the thioethers. The action of cyanogen bromide on the polypeptide molecules is selective by carrying out cleavage at the level of the existing methionine residue. This reaction leads to the formation of 2 polypeptide fragments by methionine residue. This reaction can advantageously be conjugated in particular with the previously described carboxymethylation reaction but it is not necessary for inactivation.

In other preferred conditions for the implementation of the above described process, the expected protein or the fragment is prepared conjugated to a compound allowing its purification, for example to a peptide fragment containing several histidines, preferably in a continuous sequence of 4, 5, in particular 6 histidines or more allowing fixation to a Nickel column. Insofar as the presence of this compound does not induce toxicity and does not unfavourably modify the immungenicity of the protein or fragment, it is not necessary to cleave it after purification. However, in preferred conditions of realisation, this compound is cleaved to eliminate it.

A subject of the present Application is also the use
- of a product obtained from a natural protein which is modified by any known technique such as by chemical, physical (among which is the galenic form) route or by genetic engineering, in such a way that its immunosuppressive properties are inactivated by at least 70%, preferably at least 90%, in particular at least 95%, by a chemical, physical treatment and/or by suitable genetic construction, even by suitable presentation, or
- of a DNA molecule corresponding to said protein inactivated by mutation or to said inactive fragment, for the obtaining of a pharmaceutical composition for the mucous membrane route, in particular for the mucosal route such as oral or for the intranasal route intended to give to a patient mucosal immunity, based on the secretion of secretory IgA class antibodies.

A particular subject of the Application is also the use of such products for the manufacture of a treatment by the mucous membrane route to fight immunosuppressive and/or angiogenic proteins with local activity induced in particular by a cancerous tumor or in the AIDS patient.

The modified proteins which are in particular initially immunosuppressive and/or angiogenic proteins with local activity induced by cancerous tumors in AIDS patients and the immunosuppressive properties of which are inactivated by an appropriate treatment, the fragments and the DNA molecules corresponding to these native proteins inactivated by mutation or fragments, have very useful pharmacological properties. They are endowed in particular with remarkable properties antagonist of the properties of the immunosuppressive and/or angiogenic proteins with local activity induced by a cancerous tumor by production of IgA class secretory antibodies.

These properties are illustrated hereafter in the experimental part. They justify the use of the above-described modified proteins, fragments and DNA molecules as medicaments.

In fact, the compounds according to the invention have lost their immunosuppressive properties or their angiogenic properties and can therefore be administered to man as will be seen hereafter in the experimental part.

That is why a subject of the present Application is also a pharmaceutical composition for the mucous membrane route, in particular for the oral mucous membrane route such as the intranasal or oral route containing as active ingredient a product obtained from a natural protein which is modified by any known technique such as by chemical, physical (i.e. galenic) route or by genetic engineering, in such a way that its immunosuppressive properties are inactivated by at least 70%, preferably at least 90%, in particular at least 95%, by a chemical, physical treatment and/or by appropriate genetic construction, even by appropriate presentation, or a DNA molecule corresponding to said protein inactivated by mutation or to said inactive fragment.

The medicaments according to the present invention are of use for example in the curative treatment of cancers, in particular cancers induced by viruses such as, for example, ATL (Acute T cell leukemia) caused by HTLV 1, or cervical cancer caused by the papilloma virus, or also Burkitt's lymphoma or kaposi sarcoma caused by a virus of the herpes family, Epstein-Barr (EBV) and HHV8 respectively as well as in the treatment of AIDS.

The immunogenic compounds according to the invention can be used as follows:

An immunogenic compound or a DNA molecule according to the present invention is administered to a patient in a form adapted to mucosal administration, for example by intranasal route, in a sufficient quantity to be effective on a therapeutic level, for a subject needing such treatment. The administered dose ranges for example from 10 to 1000 µg by intranasal route, once a week for two months, then periodically according to the count of secretory antibodies induced, for example every 2–6 months.

Two or more different immunogen molecules and/or DNA molecules can be administered in a same preparation to induce antibodies neutralising all the deleterious functional sites in the case where a single molecule does not carry all the active sites of the overproduced toxin or cytokine that are required to be neutralised.

A subject of the invention is also the pharmaceutical compositions intended for the mucous membranes which contain at least one above-mentioned immunogenic compound or DNA molecule, as active ingredient.

As medicaments, the immunogenic compounds or DNA molecules of the invention can be incorporated into pharmaceutical compositions intended for the mucous membrane, in particular the oral mucous membrane route, in particular the intranasal route and the oral route. Administration can take place in a single or repeated dose one or more times after a certain interval of time.

That is why a subject of the present Application is also a curative or preventive pharmaceutical composition for the mucous membrane route, characterized in that it comprises as active ingredient, one or more immunogenic compounds as defined above, or its fragments or DNA molecules corresponding to the native protein to be combated. The Immunogenic compound, fragment or DNA molecule can be conditioned on its own or mixed with a pharmaceutically acceptable excipient or mixture of excipients such as an adjuvant. Among the excipients intended for intranasal or oral route, the capryl caproyl macrogol glycerides such as Labrasol® by the company GATTEFOSSE or aluminium hydroxide (Alhydragel, Superfos, Denmark) are particularly chosen.

It should be noted that administered as it is, according to a conventional oral formulation, the active ingredient according to the invention would be inactive.

For oral administration according to the invention, the active ingredient is combined with an adjuvant of mucosal immunity such as a mutant of CT or of LT.

The galenic forms described by Boyaka et al: "Strategies for mucosal vaccine development" in Am. J. Trop. Med. Hyg. 60(4), 1999, pages 35–45 are more particularly chosen. Gastro-resistant, in particular bioadhesive microgranules such as those described by Rojas et al in Pharmaceutical Research, Vol. 16, N°2, 1999, page 255 can also be mentioned.

A more particular subject of the invention is a mucosal vaccine containing as immunogen, an immunogenic compound defined above and in particular a locally acting initially immunosuppressive and/or angiogenic protein induced by a cancerous tumor or by cells infected by a virus such as HIV or a fragment of this protein of which the immunosuppressive and/or angiogenic properties are inactivated by at least 70% by an appropriate treatment or a DNA molecule corresponding to this protein inactivated by mutation or to said inactive fragment.

In preferred conditions for implementation, a vaccinal pharmaceutical composition above is chosen, characterized in that it comprises an adjuvant of mucosal immunity, such as a mutant of CT (cholera toxin) or of LT (*E. coli* labile enterotoxin).

In other preferred conditions for implementation, a vaccinal pharmaceutical composition above is chosen, characterized in that it contains an adjuvant adsorbing the active ingredient, such as aluminium hydroxide or gold particles.

In yet more preferred conditions for implementation, a vaccinal pharmaceutical composition above is chosen, characterized in that the protein is obtained by genetic recombination and presents a peptide homology of at least 70% with the HIV-1 Tat, HTLV1 Tax or 2 and HPV E7 proteins or the mannan-dependent lectin produced by activated immune cells or with a segment of these proteins.

In yet more preferred conditions for implementation, a vaccinal pharmaceutical composition above is chosen, characterized in that the protein was treated by an aldehyde and was carboxymethylated, carboxamidated or maleimidated.

A subject of the present invention is also a process for the preparation of an above-described composition, characterized in that the active ingredient(s) are mixed, according to methods which are in themselves known, with acceptable, in particular pharmaceutically acceptable excipients and optionally, with an adjuvant of mucosal immunity.

In preferred conditions for the implementation of the above process, bioadhesive and gastro-resistant microgranules for the digestive oral route are prepared containing immunogenic active ingredients and optionally adjuvants.

Administration of immunogenic compounds according to the invention to a patient by mucosal route corresponds to active immunotherapy. It can also be useful to commence passive immunotherapy, that is to say to directly provide a patient with IgA class antibodies which they have need of to neutralise the harmful effects of the above proteins, for example immunosuppressive proteins with local activity induced by tumors.

These IgA class antibodies for example anti-immunosuppressive and/or angiogenic proteins can be obtained in a standard fashion.

That is why a subject of the present Application is also such processes for the preparation of IgA class anti-proteins in particular immunosuppressive and/or angiogenic antibodies from a cancerous tumor and in particular papilloma virus anti-E7 protein or anti-HTLV1 Tax protein antibodies, and in particular a process for the preparation of IgA class antibodies characterized above in that a mammal is immunized using an immunogenic compound as defined above, then the antibodies formed are recovered.

A subject of the present Application is also IgA class anti-immunosuppressive or angiogenic protein antibodies secreted by the cells of a cancerous tumor or infected by a virus such as HIV-1 and in particular polyclonal or monoclonal antibodies obtained from mammals immunised with an immunogenic compound defined above and in particular an immunosuppressive or angiogenic protein from a biologically inactivated but immunogenic cancerous tumor, in particular the Papilloma virus E7 protein or the HTLV1 Tax protein, or their fragments. These antibodies are administered passively, so that they are allogenic (in humans) or xenogenic (in animals) and can be complete monoclonal or polyclonal antibodies or F(ab')2 or Fab fragments of the antibodies.

By "anti-immunosuppressive or angiogenic protein antibodies of a cancerous tumor", is understood monoclonal or polyclonal antibodies or F(ab')2 or Fab fragments of these antibodies or also anti-immunosuppressive or angiogenic protein antibodies produced by the cells of a cancerous tumor or infected by HIV-1, obtained by genetic construction from a phage library.

Xenogenic antibodies originate from animals hyperimmunised with an immunogenic compound according to the invention, in particular with the Papilloma virus E7 protein or the HTLV1 Tax protein or its derivatives (peptide fragments of the detoxified Papilloma virus E7 protein or of the HTLV1 Tax protein according to the invention), and are either polyclonal originating from hyperimmunised animals, or monoclonal, obtained after hybridisation according to the Kohler and Milstein technique of spleen cells or adenocytes with a myeloma line, type x63, in particular x63AG3. In this case equine or rabbit antibodies are preferred.

A subject of the present Application is also a process for the preparation of IgA class anti-immunosuppressive or angiogenic protein antibodies of a cancerous tumor, characterized in that a mammal, man or animal is immunised by mucous membrane route, with an immunogenic compound as defined above.

A subject of the present Application is also a process of obtaining IgA class anti-immunosuppressive or angiogenic protein antibodies, by genetic recombination technology, characterized in that an immunogenic compound as defined above is used as immunogen.

A subject of the present Application is also F(ab')2 or Fab fragments of said IgA class antibodies; which can be obtained for example by enzymatic digestion.

A subject of the present invention is also a process of passive immunisation of cancer subjects or AIDS patients, using specific IgA class anti-immunosuppressive or angiogenic protein antibodies from a cancerous tumor or produced by cells infected by a virus and especially anti-Papilloma virus E7 protein or anti-HTLV1 Tax protein neutralising or blocking the harmful effects of this protein and able to be prepared as indicated above, or F(ab')2 or F(ab) fragments of these antibodies.

A subject of the present Application is also a process of active immunisation characterized in that an immunogenic compound as defined above advantageously combined with a mineral, oily adjuvant of immunity or of synthesis, or also an immunogenic compound as defined above, advantageously conjugated for example using a dialdehyde or combined with a protein increasing its immungenicity or also a DNA molecule corresponding to the protein to combat but inactivated by mutation is used as immunogen.

These immunisations can be carried out as much as a cure as a preventative treatment.

For all the above processes and hereafter, a Papilloma virus E7 protein or HTLV1 Tax protein derivative are preferably used as immunogens.

Moreover, a subject of the invention is a pharmaceutical composition for the mucosal route comprising, as a curative or preventative active ingredient, at least one IgA class anti-immunosuppressive or angiogenic protein antibody of a cancerous tumor as defined above, or obtained according to the above processes optionally combined with an IgG class anti-immunosuppressive or angiogenic protein antibody of a cancerous tumor.

In summary and in particular, a subject of the present invention is the use as a preventative, or curative treatment in the cancer subject or AIDS sufferer of IgA class antibodies in such a way as to block the action, in particular immunosuppressive action of a protein with local immunosuppressive or angiogenic action from a cancerous tumor or cells infected by a virus and in particular the HIV-1 Tat protein, the Papilloma virus E7 protein or the HTLV1 Tax protein. These specific IgA class antibodies can originate from:

1. the subject themselves, induced by active immunisation (vaccination) with a local immunosuppressive protein from a cancerous tumor secreted by cells infected by a virus deprived of said immunosuppressive effects but immunogenic (properties are preserved which are likely to induce the formation of antibodies when the protein is presented and prepared in an appropriate manner, conjugated or not to a "carrier", aggregated or not aggregated, in the presence or not of adjuvant) or with a DNA molecule corresponding to the protein to be combated but inactivated by mutation or to said inactive fragment or
2. an allo- or xenogenic foreign body, administered to the subject by passive immunisation (serotherapy). These IgA class antibodies administered passively, can be complete monoclonal or polyclonal antibodies or F(ab')2 or Fab fragments of the antibodies.

A subject of the invention is also pharmaceutical compositions and in particular a pharmaceutical composition comprising as preventative or curative agent IgA class anti-protein antibodies with a local immunosuppressive or angiogenic action from a cancerous tumor produced from organisms immunised against said protein or its F(ab')2 or Fab fragments, according to the invention.

Moreover the invention also proposes a kit comprising a vaccinal pharmaceutical composition which in addition to the active ingredient (initially immunosuppressive or angiogenic local protein from a cancerous tumor but deprived of said immunosuppressive or angiogenic effects and immunogenic, or its derivatives or local IgA class anti-immunosuppressive or angiogenic protein antibodies from a cancerous tumor or DNA molecule) can comprise an adjuvant and/or another immunogen with anti-cancer properties.

Finally the invention proposes a pharmaceutical composition adapted to mucosal administration.

To reduce the immunosuppressive charge produced by the tumor and also better improve the immune response, this anti-suppressive immunisation can be combined with immunisation by general route for example obtained by subcutaneous injection, even more classic means with as a target the reduction of the size of the tumor such as chemotherapy, radiotherapy, surgical abscission or also the addition of genes suppressive of tumors provided by gene therapy techniques (DNA carried by viral vectors, lipidic vectors etc.) or also as active immunisation against proteins without local immunosuppressive or angiogenic action such as MAGE or structural proteins such as those of the papilloma virus.

Other anti-suppressive and/or angiogenic immunisations for example in immunising against cytokines or lectins likely to serve as a mediator with suppressive action on the immune-system cell, or combined with immunisations against standard (non immunosuppressive or angiogenic) tumor antigens likely to increase the particularly fatal cell immune response (CTL cells or NK cells), directed against the cells of a tumor or infected by virus may be associated. The advantage of these combinations is that they allow the immune system to respond better to anti-immunosuppressive immunisation and as a result regenerate better.

In summary, in mucosal immunisation against a immunosuppressive or angiogenic paracrine factor present in an inactive but still immunogenic form, more standard methods can be combined such as radiotherapy, chemotherapy, surgical abscission or treatment with suppressive genes or also immunisations against cytokines or lectins produced by immune cells (T cells or APC) mediating the immunosuppressive and/or angiogenic action or against tumor antigens.

In fact, in certain cancers, even of viral origin, soluble factors of cell origin, such as cytokines or lectins can also play a role locally of mediating the immunosuppression and/or angiogenesis within tumors. This is the case with IFNα, immunosuppressive cytokine, overproduced locally within lymphoid tissues infected by HIV in the disease AIDS.

Experimentation in vitro on mononucleated blood cells (PBMC) infected by HIV-1 showed that the Tat protein was involved in overproduction by APC of IFNα immunosuppressive cytokine. Interestingly, HPV E7 like the HIV-1 Tat protein, induces the overproduction of immunosuppressive IFNα by APC.

Consequently, immune evasion and/or the angiogenesis of cancers can also be combated, by inducing or administering antibodies directed specifically against the cytokines, the overproduction of which is responsible for immunopathogenesis, in particular immunosuppression, such as IFNα and/or angiogenesis, such as TNFα conforming to International Patent Application WO 92/225.

Therefore, the immunosuppressive effects due to the overproduction of IFNα in cancers of the disease AIDS and of the cervix such as those due to the overproduction of TGFB in virally induced glioma can be blocked by antibodies directed against these natural cytokines induced by active immunisation (vaccination) using cytokinoids (modified biologically inactive but immunogenic cytokines) as a vaccine. Such antibodies can also be administered passively (passive immunisation).

The Examples and experiments which follow illustrate the present Application.

EXAMPLE 1

Preparation of Tat Carboxamide

Tat carboxamide is an inactive but immunogenic product which is prepared by carboxyamidation of the recombinant native Tat protein. Preparation of the Tat protein is in particular described in WO-A-99/33872.

The Tat toxoid was prepared in the following manner:

The recombinant native Tat protein (in solution as concentrated as possible) is dialysed for 16 hours against Tris, 0.3 M HCL buffer containing 6M guanidine and 10 mM Dithiothreitol (solution volume ratio of Tat/dialysis buffer volume: 1/20).

After dialysis, the Tat solution is collected and its volume measured. The solution is deaerated by percussion under reduced pressure. Then a deaerated solution of 0.5 M iodoacetamide acid is added by circulating a nitrogen current (in the proportions of 28 µl of 0.5 M iodoacetamide acid per ml of Tat solution).

Under nitrogen atmosphere, the reaction takes place for 90 minutes, at 37° C., sheltered from the light.

The reaction is then blocked by adding concentrated β-mercaptoethanol (0.65 µl per ml of reaction mixture).

The mixture is again placed at 37° C. for 60 minutes, sheltered from the light, under nitrogen atmosphere.

The mixture is then dialysed, under agitation, against 0.3 M HCL Tris buffer containing:

| 8 M urea: | 2 hours at ambient temperature |
|---|---|
| 4 M urea: | 2 hours at ambient temperature |
| 2 M urea: | 2 hours at ambient temperature |
| PBS 1X: | 16 hours at 4° C. |

The carboxyamidation reaction makes it possible to modify the thiol groups (sulphhydryl groups) present at the level of the cysteine residue of the amino acid sequence. These groups react with iodoacetamide acid by an S-carboxyamidomethylation reaction. The product of the reaction is an S-carboxymethylamidocysteinyl residue.

EXAMPLE 2

Preparation of Recombinant Vaccine (Lister Strain) Expressing gp160 of HIV-1 ((LAV/IIIB Strain):

Construct given by G. Beaud (Institut Jacques Monod, CNRS, Paris, France).

EXAMPLE 3 pSV-Tat Expression Plasmid

The pSV-Tat expression plasmid was amplified in *E. Coli* and purified by centrifugation in cesium chloride (Advanced Biotechnologies Inc.).

The immunogenic compounds of examples 1, 2 and 3 were combined with an adjuvant in order to potentiate the immune response.

The Adjuvants

Different types of adjuvant were tested:
 mutated thermolabile toxin (mutated L.T) of enterotoxigen *Escherichia coli* (ETEC): LT (R192G) described by Cardenas-Freytag L et al, Effectiveness of a vaccine composed from heat-killed Candida albicans and a novel mucosal adjuvant, LT (R192G), Against systemic candidiasis, Infect immun; 1999, 67:826–33.
 sub-unit B (CTB) of cholera toxin (CT) of Vibro cholerae bacteria contaminated by total CT.
 Montanide IMS 1113,
 C92512,
 ISA 51. (SEPPIC).

EXAMPLE 4

An intranasal solution was prepared corresponding to formula compound of Example 2 . . . 10 mg excipient in a sufficient quantity for an intranasal solution finished at . . . 20 ml (detail of the excipient: Labrasol®, sodium chloride, sodium benzoate, water for injectable preparations).

EXAMPLE 5

An intranasal solution was prepared corresponding to formula Tat carboxymethyl described in WO-A-99/33872 . . . 10 mg excipient in a sufficient quantity for an intranasal solution finished at . . . 20 ml detail of the excipient: Labrasol®), sodium chloride, sodium benzoate, water for injectable preparations).

EXAMPLE 6

Oral capsules were prepared each containing:
Compound of Example 1 . . . 200 µg
Alhydrogel by Superfos . . . 20 µg
Oral excipient in a sufficient quantity . . . 0.5 ml Pharmacological Study Experiment 1

Protocol: mice received 100 µl of emulsion (1:1) by intramuscular route, in ISA 51 containing 25 µg of Tat carboxamide of Example 1 and 5 µg of LT on day 0. Then, on days 7, 14 and 21, these mice received 10 to 15 µl of a preparation containing 25 µg of Tat carboxamide of Example 1 and 3 µg of LT by intranasal route. Serum from these mice was removed on day 28.

Research of anti-Tat antibodies, of IgG and IgA type in their serum was carried out by the following ELISA test: plates are sensitised with Tat carboxamide (1 µg/well). The serums, diluted by ¼ to detect type IgA antibodies or diluted by ¹⁄₅₀ for IgG type antibodies, are tested according to standard ELISA protocols. The results obtained are expressed in O.D.

| | Class | Mice Controls | Immunised mice |
|---|---|---|---|
| Ac. Anti-Tat | IgG | 0.175 | 2.224 |
| Ac. Anti-Tat | IgA | 0.461 | 1.759 |

This immunisation protocol a leads to an increase in the count of specific IgG and IgA class antibodies, providing both systemic and mucosal immunity, confirmed by the presence of secretory IgA's in washes of intestinal secretions carried out according to the technique of Elson C. V. et al. (J. of Immunol Methods, 1984, 67: 101–108).

Experiment 2

Protocol: mice received 10 to 15 µl of emulsion (1:1), in IMS 1113 or C92512, containing 25 µg of Tat carboxamide and 5 µg of LT by intranasal route on day 0. Then, on days 7 and 14, these mice received 10 to 15 µl of emulsion (1:1), in IMS 1113 or in C92512 respectively, containing 25 µg of Tat toxoid and 3 µg of LT by intranasal route. Serum from these mice was removed on day 21. Research of anti-Tat antibodies, of IgG and IgA type in their serum was carried out by the ELISA test described in the protocol of experiment 1.

| | Class | Mice Controls | Immunised mice (C92512) | Immunised mice (IMS 1113) |
|---|---|---|---|---|
| Ac. Anti-Tat | IgG | 0.2 | 2.220 | 1.543 |
| Ac. Anti-Tat | IgA | 0.7 | 0.7 | 1.092 |

The use of IMS 1113 adjuvant (Seppic, France) made it possible to induce mucosal immunity, characterized by amplification of the count of IgA class anti-Tat antibodies. On the other hand, the addition of C92512 adjuvant (Seppic, France) is not permitted.

Experiment 3

Protocol: mice received 10 to 15 µl of a preparation containing 10 µg of the plasmid of Example 3, 5 µg/ml of CTB and 5 µg/ml of CT by intranasal route on day 0. Then, on days 7 and 14, these mice received 10 to 15 µl of a preparation containing 25 µg of Tat toxoid and 5 µg/ml of CTB and 0.5 µg/ml of CT by intranasal route. Serum from these mice was removed on day 21. Research of anti-Tat antibodies, of igG and IgA type in their serum was carried out by the ELISA test described in the protocol of experiment 1.

|  | Class | Mice Controls | Immunised mice |
|---|---|---|---|
| Ac. Anti-Tat | IgG | 0.3 | 2.123 |
| Ac. Anti-Tat | IgA | 0.2 | 1.951 |

Immunisation by intranasal route using anti-Tat plasmid characterized by an increase of IgA and confirmed by the presence of Secretory IgA's in the intestinal secretions.

Experiment 4

Protocol: mice have received 200 µl of a preparation containing $10^6$ PPU/ml of recombinant vaccine expressing gp160, 5 µg/ml of CTB and 0.5 µg/ml of CT by oral route on days 0, 7 and 14. Serum from these mice was removed on day 21.

Research of anti-Tat antibodies, of IgG and IgA type in their serum was carried out by the following ELISA test: plates are sensitised with native recombinant gp160 (1 µg/puits). The serums, diluted to ¼ to detect type IgA antibodies or diluted to ⅟50 for the IgG type antibodies, are tested according to standard ELISA protocols. The results obtained are expressed in O.D.

|  | Class | Mice Controls | Immunised mice |
|---|---|---|---|
| Ac. Anti-gp160 | IgG | 0.112 | 1.283 |
| Ac. Anti-gp160 | IgA | 0.440 | 1.02 |

The increase of IgG and IgA class antibodies reflects both systemic and mucosal anti-gp160 immunity.

Experiment 5

Protocol: mice received on days 0, 7, 14 and 21, 10–15 µl of PBS containing as immunogen 50 µg of Tat carboxamide of Example 1 and as adjuvant LT (3–5 µg) and 2 µl of aluminium hydroxide (Alhydrogel 85 from Superfos Biovector, Denmark) by intranasal route. The search for IgG and IgA type anti-Tat antibodies in their serums was carried out by ELISA following the protocol of Example 1.

|  | Class | Mice Controls | Immunised mice |
|---|---|---|---|
| Ac. Anti-Tat | IgG | 0.182 | 2.042 |
| [2]Ac. Anti-Tat | IgA | 0.461 | 1.258 |

The aggregation of the Tat Toxoid immunogen around particles of aluminium hydroxide in the presence of LT facilitates the anti-Tat antibody response.

The invention claimed is:

1. A method for inducing a mucosal immunity with production of secretory IgA antibodies that neutralize or block a native Tat protein originating from cancerous cells, from cells infected by an HIV virus or from an immune system cell, said native Tat protein being locally immunosuppressive and/or angiogenic and said method comprising administering to a patient in need thereof, by the mucous membrane route, a pharmaceutical composition comprising:
(i) an active compound selected from the group consisting of:
said immunosuppressive and/or angiogenic native Tat protein, the properties of which have been inactivated by at least 70% by a physical and/or a chemical treatment, by genetic recombinant or also by adjuvant conditioning;
an inactive fragment of said immunosuppressive and/or angiogenic native Tat protein;
a DNA molecule encoding said immunosuppressive and/or angiogenic native Tat protein inactivated by at least 70% by mutation; and
a DNA molecule encoding an inactive fragment of said immunosuppressive and/or angiogenic native Tat protein; and
(ii) an adjuvant of mucosal immunity.

2. The method of claim 1, wherein said active compound consists of said immunosuppressive and/or angiogenic native Tat protein that has been chemically treated with a chemical reagent selected from the group consisting of an aldehyde, a carboxamide, a carboxymethyl or a maleimide.

3. The method of claim 1, wherein said active compound consists of a protein mutant from said immunosuppressive and/or angiogenic native Tat protein.

4. The method of claim 1, wherein said active compound consists of a DNA molecule encoding (i) said immunosuppressive and/or angiogenic native Tat protein inactivated by at least 70% by mutation or (ii) an inactive fragment of said immunosuppressive and/or angiogenic native protein.

5. The method of claim 1, wherein the properties of said immunosuppressive and/or angiogenic native Tat protein have been inactivated by at least 70% by a chemical treatment and wherein said chemical treatment is selected from the group consisting of formolation, carboxamidation, carboxymethylation, maleimidation or oxidation by oxygen bubbling.

6. The method of claim 1, wherein the mucous membrane route is an oral mucous membrane route.

* * * * *